United States Patent
Appel et al.

(10) Patent No.: US 7,354,553 B2
(45) Date of Patent: Apr. 8, 2008

(54) METHOD AND APPARATUS FOR DETECTING THE PRESENCE OF ELEMENTAL MERCURY IN A GAS SAMPLE

(76) Inventors: Dirk Appel, 25 Chestnut St., Salem, MA (US) 01970; James H. Grassi, 191 Pond St., Westwood, MA (US) 02090; Dieter Kita, 7 Susan Dr., Blackstone, MA (US) 01504; Jeffrey Socha, 280 Randall Rd., Berlin, MA (US) 01503

(*) Notice: Subject to any disclaimer, the term of this patent is extended or adjusted under 35 U.S.C. 154(b) by 165 days.

(21) Appl. No.: 11/120,317

(22) Filed: May 2, 2005

(65) Prior Publication Data

US 2006/0246594 A1    Nov. 2, 2006

(51) Int. Cl.
G01N 33/20 (2006.01)
G01N 21/64 (2006.01)
G01J 3/443 (2006.01)

(52) U.S. Cl. .............. 422/91; 250/339.12; 250/339.13; 250/343; 250/364; 250/365; 250/373; 250/432 R; 250/461.1; 250/573; 356/246; 356/436; 356/437; 356/438; 356/439; 422/52; 422/82.02; 422/83; 436/73; 436/81; 436/172; 436/182

(58) Field of Classification Search ................ 250/339.12–339.13, 343, 364–365, 373, 250/432 R, 458.1, 461.1, 573; 356/246, 356/436–444; 422/52, 82.08, 83, 91; 436/73, 436/81, 172, 182

See application file for complete search history.

(56) References Cited

U.S. PATENT DOCUMENTS 3,528,779 A * 9/1970 Fontijn ................ 436/135
3,635,561 A * 1/1972 Bordonali et al. ........ 356/311

(Continued)

FOREIGN PATENT DOCUMENTS

WO        97/29360      * 8/1997

OTHER PUBLICATIONS

Thompson, K. C. et al, Analyst 1971, 96, 771-775.*

(Continued)

*Primary Examiner*—Arlen Soderquist
(74) *Attorney, Agent, or Firm*—Chapin IP Law, LLC; Barry W. Chapin, Esq.

(57) ABSTRACT

An improved elemental mercury analyzer utilizes a fluorescence assembly in combination with a fluorescence quenching reduction mechanism to detect the concentration of elemental mercury within an emission gas sample, via fluorescence of the mercury within the gas sample, while minimizing fluorescence quenching of the gas sample. In one arrangement, the analyzer contains the emission gas sample under a vacuum or negative pressure while detecting fluorescence of the elemental mercury within the emission gas sample. By performing fluorescence detection of the emission gas sample at reduced pressure relative to the pressure of the as-sampled emission gas, the analyzer reduces the number of particle collisions within the emission gas sample over a certain period of time. Such collisional deactivation, and/or the addition of oxygen depleted gas such as nitrogen to the gas sample, reduces fluorescence quenching of the emission gas sample, improving accuracy of detection of mercury.

10 Claims, 6 Drawing Sheets

U.S. PATENT DOCUMENTS

| | | | | |
|---|---|---|---|---|
| 3,763,877 | A * | 10/1973 | Lieb | 137/115.09 |
| 3,805,077 | A * | 4/1974 | D'Silva et al. | 250/372 |
| 3,826,920 | A * | 7/1974 | Woodroffe et al. | 250/373 |
| 3,858,980 | A * | 1/1975 | West | 356/312 |
| 3,897,155 | A * | 7/1975 | Smythe | 356/317 |
| 4,309,187 | A * | 1/1982 | Dodge et al. | 436/35 |
| 4,391,776 | A * | 7/1983 | Braun | 422/78 |
| 4,432,644 | A * | 2/1984 | Demers et al. | 356/316 |
| 4,645,341 | A * | 2/1987 | Koga et al. | 356/307 |
| 4,660,976 | A * | 4/1987 | Falk | 356/312 |
| 5,597,535 | A * | 1/1997 | Schaedlich et al. | 422/88 |
| 5,619,041 | A * | 4/1997 | Hoffmann et al. | 250/373 |
| 5,679,957 | A * | 10/1997 | Durham et al. | 250/373 |
| 5,750,992 | A * | 5/1998 | Van Pelt et al. | 250/372 |
| 5,879,948 | A * | 3/1999 | Van Pelt et al. | 436/81 |
| 5,900,042 | A | 5/1999 | Mendelsohn et al. | 75/742 |
| 6,475,802 | B2 * | 11/2002 | Schaedlich et al. | 436/81 |
| 6,589,795 | B2 * | 7/2003 | Tyson et al. | 436/81 |
| 6,852,542 | B2 | 2/2005 | Mandel et al. | 436/81 |
| 7,037,725 | B2 | 5/2006 | Mandel et al. | 436/81 |
| 2002/0068030 | A1 | 6/2002 | Nolan et al. | 423/210 |

OTHER PUBLICATIONS

Pchelintsev, A. M. et al, International Congress on Atomic Absorption and Atomic Fluorescence Spectrometry, Pap., 3rd 1973, vol. 1, 283-288, Publisher: Wiley, New York, N. Y.*

Karyakin, A. V. et al, Zhurnal Analiticheskoi Khimii 1976, 31, 236-239.*

Koizumi, H. et al, Analytical Chemistry 1977, 49,1106-1112.*

Nakahara, T. et al, Bulletin of the Chemical Society of Japan 1978, 51, 2020-2024.*

Ebdon, L. et al, Analytica Chimica Acta 1981, 128, 45-55.*

Frueholz et al, Chemical Abstracts 1984, 101, abstract 103115.*

Bolshov, M. A. et al, Spectrochimica Acta 1986, 41B, 487-492.*

Womack, J. B. et al, Spectrochimica Acta 1991, 46B, 301-308.*

Corns, W. T. et al, Journal of Automatic Chemistry 1991, 13, 267-271.*

Chan, C. C. Y. et al, Analytica Chimica Acta 1993, 282, 109-115.*

Lonardo, R. F. et al, Analytical Chemistry 1996, 68, 514-521.*

Bahns, J. T. et al, Optics Letters 1997, 22, 727-729.*

Morrison, M. A. et al, Applied Organometallic Chemistry 1997, 11, 761-769.*

Blois, A. J. et al, Analytical Chemistry 1998, 70, 1223-1227.*

Bramanti, E. et al, Journal of Analytical Atomic Spectrometry 1999, 14, 179-185.*

Tong, X. et al, Environmental Science and Technology 1999, 33, 3260-3263.*

Bauer, D. et al, Journal of Environmental Monitoring 2002, 4, 339-343.*

Tong, X. et al, Review of Scientific Instruments 2002, 73, 2392-2397.*

Yan, X.-P, et al, Analytical Chemistry 2003, 75, 1726-1732.*

Thompson, K. C. et al, Analyst 1975, 100, 544-548.*

Kvietkus, K. et al, Fizika Atmosfery 1983, 8, 127-131.*

Godden, R. G. et al, Journal of Analytical Atomic Spectrometry 1989, 4, 301-303.*

D'ulivo, A. et al, Analytical Letters 1997, 30, 2109-2122.*

Khvostikov, V. A. et al, Journal of Analytical Chemistry 2003, 58, 519-523.*

Frueholz, R.P.; Gelbwachs, J.S., Chem. Phys. Lab., aerospace Corp., Los Anegeles CA 90009, USA., Spectrochim Acta, Part B, 39B(6), 807-12, 1984 Polarization rejection of scattered incident laser light in resonance fluorescence flame atomic detection.

* cited by examiner

METHOD AND APPARATUS FOR DETECTING THE PRESENCE OF ELEMENTAL MERCURY IN A GAS SAMPLE

RELATED APPLICATIONS

This application relates to U.S. patent application Ser. No. 11/120,315 entitled "METHOD AND APPARATUS FOR CONVERTING OXIDIZED MERCURY INTO ELEMENTAL MERCURY", U.S. patent applications Ser. No. 11/120,316, entitled "METHOD AND APPARATUS FOR GENERATING OXIDIZED MERCURY HAVING A MEASURABLE CONCENTRATION", and U.S. patent application Ser. No. 11/120,182, entitled "METHOD AND APPARATUS FOR MONITORING MERCURY IN A GAS SAMPLE", all filed on even date herewith, the entire teaching of which are incorporated herein reference.

FIELD OF THE INVENTION

Embodiments of the present invention relate to the detection of mercury in fossil fuel emissions and, more particularly, to the use of fluorescence detection in combination with a mechanism to reduce fluorescence quenching as well as reduce background signal due to scattering of excitation energy by the gas sample, in order to detect the presence of mercury within fossil fuel emissions.

BACKGROUND

Emissions from fossil fuel combustion facilities, such as flue gases of coal-fired utilities and municipal solid waste incinerators, typically include mercury. The emissions include vaporized mercury as elemental mercury, $Hg^0$ as well as oxidized forms of mercury ($Hg^{+2}$), such as in mercuric chloride or mercuric nitrate.

Many countries regulate or are contemplating regulations of emissions of mercury within waste gases because of potential environmental hazards posed by the mercury emissions. Hence, facilities that generate gas emissions that can contain mercury typically would monitor total mercury concentration in the emissions to comply with the regulations. For example, mercury monitoring systems can convert oxidized mercury to elemental mercury and then use atomic fluorescence spectroscopy to detect the elemental mercury. In atomic fluorescence spectroscopy, a spectrometer detects a concentration of a particular chemical species (e.g., an element or molecule) in a sample by measuring the degree to which that particular species absorb light of a wave-length which characterizes the species.

For example, to detect mercury within a gas emission sample, a light source emitting light at 253.7 nm is used to excite mercury atoms within a sample. As the elemental mercury within the gas sample absorbs the light from the light source, the elemental mercury enters an excited state. As the excited elemental mercury decays from the excited state back to a non-excited state, the elemental mercury releases energy by fluorescing light. A detector measures the light fluorescence produced by the sample. The fluorescence represents a measure of the concentration of the elemental mercury in the gas sample.

Certain conventional elemental mercury detectors utilize cold-vapor atomic absorption spectrometry (CVAAS) or cold-vapor atomic fluorescence spectrometry (CVAFS) as detection techniques. The CVAAS and CVAFS detection techniques, however, are susceptible to measurement interferences such as caused by interference gases (e.g., $NO_x$, $SO_2$, HCl, and $Cl_2$) or quenching gases e.g., $N_2$, $O_2$, present within a sample. Elemental mercury detectors utilizing CVAAS or CVAFS detection techniques benefit from the removal of these interference gasses.

In the CVAAS technique, gases (e.g., $NO_x$, $SO_2$, HCl, and $Cl_2$) may cause interference with the measurements made by associated elemental mercury detectors. The gasses absorb light during use of the CVAAS measurement technique. Thus, conventional elemental mercury detectors using the CVAAS measurement technique can provide a false reading. To minimize or remove interference gasses for detectors using the CVAAS technique, for example, elemental mercury detectors utilize a gold trap to minimize or remove the effects of $SO_2$ within a gas sample. The gas sample flows, over time, through the gold trap, the gold material traps elemental mercury present within the gas sample. After the gold trap collects elemental mercury over time, the gold trap is heated and a $SO_2$-free carrier gas is passed over the gold trap to deliver the elemental mercury collected on the gold trap to the detector. The gold trap, therefore, limits the effect of $SO_2$ on the absorption of the elemental mercury and improves measurement sensitivity of the CVAAS detector.

For elemental mercury detectors using the CVAFS technique, fluorescence quenching by gases (e.g., $N_2$, $O_2$) can affect the performance of the detectors. In the CVAFS technique, concentrating devices, such as gold traps, are used to minimize or remove the effect of fluorescence quenching on the measurements made by the detectors. The trap collects elemental mercury over time and maximizes the detection sensitivity of the associated detector. The trapped mercury is then thermally desorbed into a gas stream of Argon, which is a much less efficient quencher than either nitrogen or oxygen. Thus the gas sample can be conditioned to minimize the presence ands effect of fluorescence quenching gases (e.g., $N_2$, $O_2$) on the measurements made by the detector using the CVAFS technique.

SUMMARY

Conventional mechanisms and techniques that use fluorescence to detect the concentration of the elemental mercury in gas emission samples have deficiencies, as described below.

As indicated above, in atomic fluorescence spectroscopy, as elemental mercury within a gas sample absorbs light from a light source (e.g., where the light source of the spectrometer emits light of a relatively narrow wavelength corresponding to the atomic absorption of the elemental mercury), the elemental mercury enters an excited state. As the excited elemental mercury moves from the excited state back to a non-excited state, the elemental mercury releases energy in the form of fluoresced light. However, a process known as "fluorescence quenching" reduces the detectable fluorescence of the elemental mercury.

The mechanism that causes fluorescence quenching is collisional deactivation. In collisional deactivation, an excited mercury atom collides with another atom/molecule within the gas emission sample or with a wall of the spectrometer, and transfers energy with the object of the collision. In so doing, the excited elemental mercury atom surrenders its energy through a non-fluorescent mechanism (i.e., without emitting light). Collisional deactivation reduces the overall fluorescence intensity of the elemental mercury present within the gas sample. Thus, fluorescence quenching can reduce the ability of an atomic fluorescence spectrometer to accurately measure the concentration of elemental mercury in the gas sample.

While collisional deactivation of electronically excited mercury is a general phenomena, particular molecules are more efficient than others in bringing about non-fluorescence deactivation. Oxygen is particularly efficient quenching agent. By diluting the sample stream with an oxygen-depleted carrier gas or removing the oxygen through combustion or some other means, the effects of oxygen quenching are minimized and the signal enhanced relative to what would be observed should oxygen be present in the same volume of carrier gas.

Additionally, as described above, certain elemental mercury detection systems, such as those utilizing cold-vapor atomic absorption spectrometry (CVAAS) or cold-vapor atomic fluorescence spectrometry (CVAFS) as detection techniques, collect elemental mercury within a gas emission sample by trapping the elemental mercury on gold material, over a particular time period. At the conclusion of the time period, the elemental mercury detector desorbs the collected, concentrated mercury from the trap and the concentration of mercury within the gas emission sample is detected using a spectrometer. While such a system allows detection of the concentration of mercury within the gas sample, the detection is part of a "batch process" and is not continuous. Thus the described elemental mercury detection system is less likely, depending upon the timing of the batch process, to detect irregularities or changes in the mercury concentration within the gas sample at a particular instant (e.g., "spikes" in the mercury concentration at a particular time or for a particular duration). The described elemental mercury detector instead detects the time averaged mercury concentration for the gas sample.

By contrast to conventional analyzers, an elemental mercury analyzer of the present invention utilizes a fluorescence assembly in combination with a fluorescence quenching reduction mechanism, which minimizes or reduces the effect of quenching on the fluorescence of the elemental mercury. In one arrangement, the analyzer maintains the emission gas sample under a vacuum or negative pressure while detecting fluorescence of the elemental mercury within the gas sample. By reducing the pressure of the emission gas sample during fluorescence detection, the analyzer reduces the sample density and therefore the number of particle collisions within the emission gas sample during detection, thereby reducing fluorescence quenching of the excited elemental mercury within the emission gas sample relative to atmospheric pressure. In another arrangement, a carrier/dilution gas with little or no oxygen is mixed with the sample gas prior to analysis. By reducing the presence of oxygen, the relative emission signal is increased hence facilitating mercury detection.

In one arrangement, an elemental mercury analyzer has a housing with an inlet for receiving a fluid sample (e.g., a gas sample) from a fluid source, an outlet for discharging the fluid sample, and the housing defines a chamber for containing the fluid sample. The elemental mercury analyzer also has a fluorescence assembly in optical communication with the chamber for inducing fluorescence of elemental mercury present within the fluid sample and for detecting a fluorescence signal upon fluorescence of at least a portion of the elemental mercury. The elemental mercury analyzer also has a fluorescence quenching reduction mechanism in fluid communication with the chamber to reduce or minimize the effect of quenching on the fluorescence of the fluid sample. The fluorescence quenching reduction mechanism thus improves or enhances accuracy of detection of elemental mercury in the fluid sample.

In one arrangement, the fluorescence quenching reduction mechanism includes a pressure reduction apparatus coupled to the housing of the elemental mercury analyzer. The pressure reduction apparatus reduces the pressure of the fluid sample, relative to that of the fluid source, to minimize the effect of collisional deactivation on the fluorescence of the elemental mercury within the fluid sample.

In one arrangement, the fluorescence quenching reduction mechanism of the elemental mercury analyzer includes a source of oxygen depleted gas in fluid communication with the chamber of the analyzer. The oxygen depleted gas acts to reduce the relative fluorescence quenching effect caused by oxygen gas present within the fluid sample.

In one arrangement, the fluorescence quenching reduction mechanism of the elemental mercury analyzer includes a combination of both a pressure reduction apparatus and an oxygen depleted gas source. The combination of the pressure reduction apparatus and the oxygen depleted gas source reduces the effect of quenching on the fluorescence of elemental mercury within a gas sample.

BRIEF DESCRIPTION OF THE DRAWINGS

The foregoing and other objects, features and advantages of the methods and apparatus will be apparent from the following description of particular embodiments, as illustrated in the accompanying drawings in which like reference characters refer to the same parts throughout the different views. The drawings are not necessarily to scale, emphasis instead being placed upon illustrating the principles of the apparatus.

DETAILED DESCRIPTION

An improved elemental mercury analyzer utilizes a fluorescence assembly in combination with a fluorescence quenching reduction mechanism to detect the concentration of elemental mercury within an emission gas sample, via fluorescence of the mercury within the gas sample, while minimizing the effect of fluorescence quenching. In one arrangement, the analyzer contains the emission gas sample under a vacuum or negative pressure while detecting fluorescence of the elemental mercury within the emission gas sample. By reducing the pressure of the emission gas sample during fluorescence detection, the analyzer reduces the number of particle collisions within the emission gas sample and hence reduces the fluorescence quenching of elemental mercury within the emission gas sample. In another arrangement, the analyzer introduces or adds an oxygen depleted gas to the emission gas sample. The presence of oxygen depleted gas within the emission gas sample reduces the tendency of oxygen to quench the fluorescence signal generated by elemental mercury within the emission gas sample.

Figure 1:
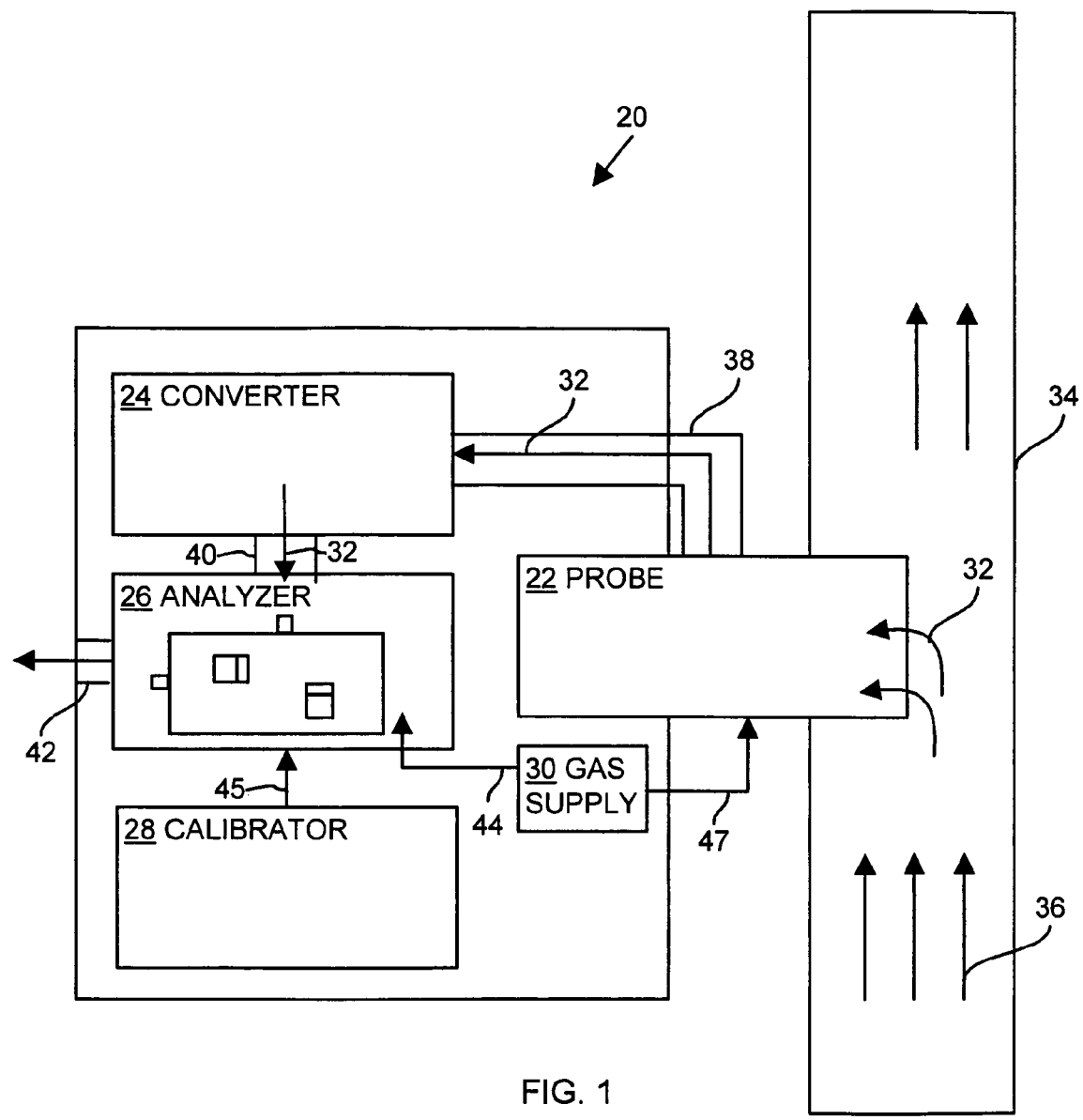
FIG. 1 is a schematic of a mercury monitoring system.

FIG. 1 illustrates a mercury monitoring system 20 for monitoring total mercury within a fluid sample, such as in an effluent gas from a coal-fired power plant, in a substantially continuous manner. The mercury monitoring system 20, or Continuous Emission Monitoring System (CEMS), includes a probe 22, a converter 24, an analyzer 26, a calibrator 28, and a gas supply 30.

The probe (e.g., extraction probe) 22 is configured to receive a fluid sample 32 from a sample source and deliver the fluid sample 32 to the converter 24. For example, the probe 22 extends into, or is mounted proximate to, a stack or flue 34 of a coal combustion facility and collects, as the gas sample 32, a portion of the fluid or gas (e.g., effluent) 36 flowing through the stack 34. The probe 22, in one arrangement, includes an inertial filter that separates particulate matter (e.g., flue ash) from the gas sample 32. Surfaces of the probe 22 that contact the gas sample 32 typically have a coating (e.g., glass) that minimizes or prevents chemical reactions between the probe and mercury present within the gas sample 32.

The probe 22 is connected to the converter 24 by way of a heated conduit 38 maintained at a temperature of, for example, 150° C. The heated conduit 38 limits condensation of the gas sample 32 and "sticking" of vaporized mercury to the conduit 38 and provides efficient transport of the gas sample 32 to the converter. The probe 22 couples to the gas supply 30 via a conduit 47. In one arrangement, the gas supply 30 provides dilution gas, such as air, to the probe 22 to dilute the concentration of mercury within the gas sample 32 prior to delivery of the gas sample 32 to the converter 24. The converter 24 receives the gas sample 32 from the probe 22 and is operable to convert the vapor-phase species of mercury (e.g., oxidized mercury) present within the gas sample 32 into elemental mercury and to maintain the mercury in the elemental form so as to allow the analyzer 26 to detect the total mount of mercury present within a gas sample.

The analyzer 26 is connected to the converter 24 by way of a heated conduit 40 (e.g., heated, for example, to a temperature of between 100° C. and 200° C.) and receives the heated and reduced pressure gas sample 32 from the converter 24. In one arrangement, the analyzer 26 is an atomic fluorescence analyzer that measures or detects an amount or a concentration of elemental mercury present within the gas sample 32. Upon completion of the detection process, the analyzer 26 exhausts the fluid or gas sample 32 to the atmosphere via an exhaust port 42. A more detailed description of the analyzer 26 is provided below.

Typically, the analyzer 26 requires periodic calibration in order to accurately detect or measure the presence of elemental mercury within a gas sample 32. Calibration is provided by the calibrator 28 which, in one arrangement is in fluid communication with the analyzer 26 through a line or conduit 45 and provides vaporized elemental mercury to the analyzer 26 at a particular concentration, such as by using a Peltier cooler/vapor pressure control and mass flow controllers. The analyzer 26 compares the amount of elemental mercury received from the calibrator 28 with that of dry, substantially mercury-free gas (e.g., zero air), received from the gas supply 30 via conduit 44. The results of such a comparison allow direct calibration of the analyzer 26.

The system 20 monitors total mercury within a gas sample 32 in a substantially continuous manner. Generally, the elemental mercury analyzer 26, such as used within the system 20, is configured to receive a fluid sample 32, such as a gas sample 32 containing vaporized mercury, and detect the fluorescence of the elemental mercury within the sample. The elemental mercury analyzer 26 utilizes a mechanism, such as a fluorescence quenching reduction mechanism, to reduce the effect of fluorescence quenching on the fluorescence of the elemental mercury within the sample 32. By reducing the effect of fluorescence quenching, the analyzer 26 provides substantially accurate measurement of the concentration of the elemental mercury in the gas sample 32.

Figure 2:
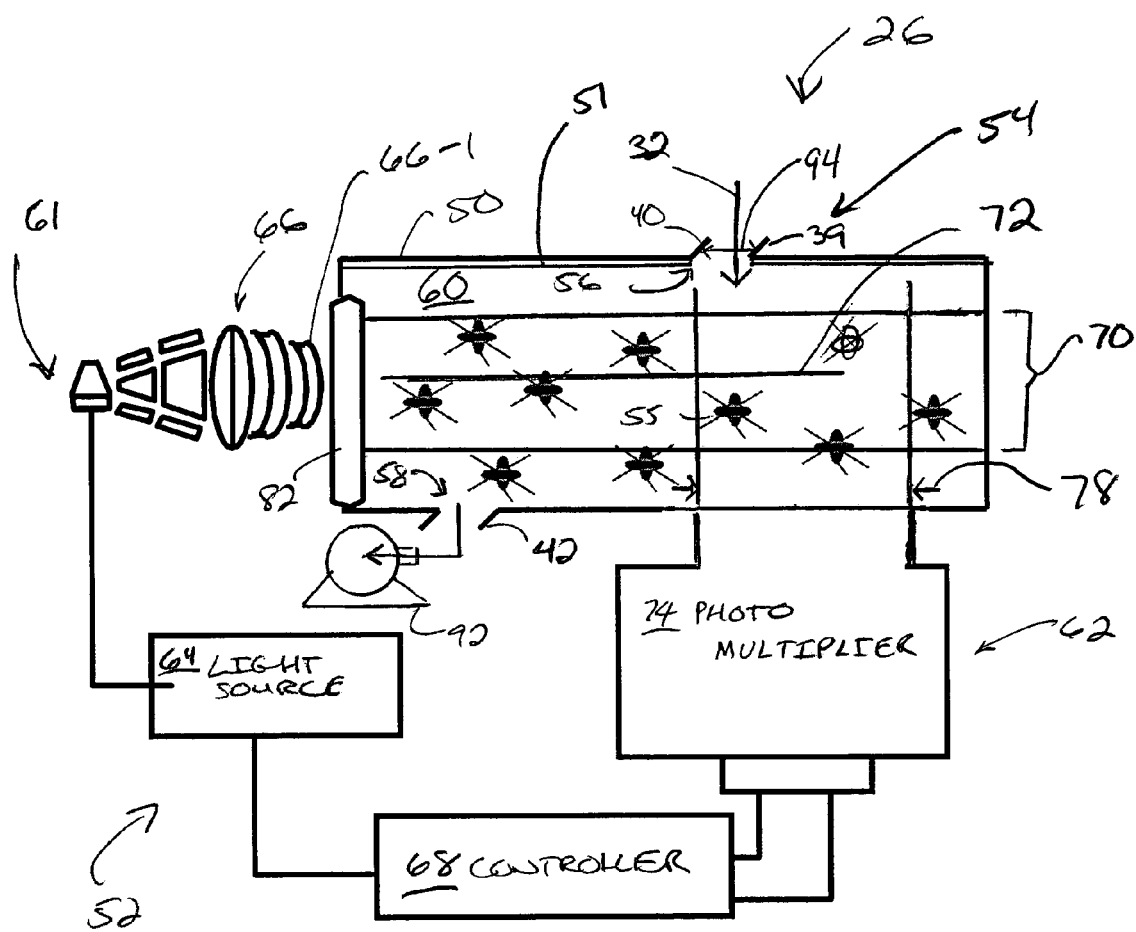
FIG. 2 illustrates an arrangement of a mercury analyzer as used within the mercury monitoring system of FIG. 1.

FIG. 2 illustrates an arrangement of the elemental mercury analyzer 26. The analyzer 26 includes a housing 50, a fluorescence assembly 52, and a fluorescence quenching reduction mechanism.

The housing 50 has an inlet 56, an outlet 58, and defines a chamber 60. The inlet 56 is configured to receive a fluid sample 32 from a fluid source, such as the converter 24 as shown in FIG. 1, via the conduit 40. The outlet 58 is configured to discharge or exhaust the fluid or gas sample 32 to the atmosphere via the exhaust port 42. The chamber 60 is configured to contain the fluid sample 32, such as a gas emissions sample, during analysis of the sample. In one arrangement, light baffling material 51 is included within the chamber 60 to minimize scattering of light within the chamber 60.

The fluorescence assembly 52 includes a light source assembly 61 and a detector assembly 62 in optical communication with the chamber 60 and hence with a fluid sample 32 contained by the housing 50. The fluorescence assembly 52 induces fluorescence of elemental mercury 55 present within the fluid sample 32 and detects a fluorescence signal of the fluid sample 32 based upon fluorescence of the elemental mercury.

The light source assembly 61, in one arrangement, includes a light source 64 and lenses 66. The light source 64, in one arrangement, is a high-intensity mercury lamp, which produces light at a wavelength of approximately 253.7 nm and delivers the light to the lenses 66. The lenses 66, in turn, direct the light from the light source 64 to the chamber 60. As the lenses 66 direct the light from the light source 64 into the chamber 60, the light (e.g., having the wavelength of approximately 253.7 nm) excites elemental mercury 55 located within the chamber 60. As a result of the excitation, the elemental mercury 55 releases energy, such as via fluorescence.

The detector assembly 62, in one arrangement, includes a photo multiplier tube 74 electrically coupled to the controller 68. The photo multiplier tube 74 is in optical communication with the chamber 60 of the housing 50 and is operable to receive and detect light fluoresced by the elemental mercury 55 within the chamber 60. As the photo multiplier 74 receives a fluorescence signal from the fluid sample (e.g., fluoresced light from the elemental mercury 55), the photo multiplier 74 generates a signal proportional to the fluorescence signal (e.g., proportional to the intensity of the fluorescence of the elemental mercury 55 within the gas sample 32) and transmits the signal to a controller 68. The controller 68 (e.g., its memory and processor) calculates or detects the concentration of the elemental mercury 55 in the gas sample 32 based upon the signal received from the photo multiplier 74.

In one arrangement, the analyzer 26 utilizes a polarizing element in conjunction with the light source assembly 61 and the detector assembly 62 to improve detection of the signal of the fluoresced light from the elemental mercury 55 and, ultimately, the signal-to-noise ratio of the detector assembly 62.

For example, the light source assembly 61 includes a polarizing element or filter 82 positioned between the lenses 66 and the chamber 60 of the housing 50. The polarizing filter 82 polarizes the incident light from the lenses 66 to reduce an amount of scattered light 60 observed by the detector. The polarizing filter 82 is oriented to pass only the plane of light orthogonal to the plane of light transmitted by light scattering thereby reducing the amount of scattered light within the chamber 60.

During operation, the polarizing filter 82 polarizes incident light emitted from the lenses 66 entering the chamber 60 to remove the plane of light transmitted by light scattering. As the polarized incident light travels through the chamber 60, the polarized light can become scattered (e.g., as caused by interaction between the polarized light and the walls of the housing 50 or particulate matter in the fluid sample 32 contained by the housing 50). The light scatter resulting from particle interaction favors one of two orthogonal planes, depending on the orientation of the polarizing element 82 and the detector 62. By transmitting only an unfavorable plane of light (e.g., the plane of light orthogonal to the plane of light transmitted by light scattering) into the fluorescing chamber 60, the amount of scattered light is reduced within the chamber 60. A reduction in scattered light enhances the detector's 62 ability to monitor mercury. The elemental mercury 55 fluoresces light as non-polarized light. Therefore, the use of polarized light, 84 improves detection of the signal of the fluoresced light from the elemental mercury 55 and provides the detector assembly 62 with an enhanced or improved fluorescence detection limit.

As indicated above, when polarized incident light travels through the chamber 60, the polarized light can become scattered. Typically, scattered light observed at a right angle to the direction of propagation of the polarized incident light is plane polarized.

In one arrangement, the polarizing filter 82 of the light source assembly 61 directs polarized incident light along a first axis or optical orientation 72 within the chamber 60. For example, the first optical orientation 72 is substantially perpendicular (e.g., at a substantially 90 degree angle) to a face of the polarizing filter 82 while the scattered light is substantially parallel to the face of the polarizing filter 82.

During operation, polarized incident light traveling along the first optical orientation 72 causes elemental mercury 55 present within a first optical zone 70 to fluoresce. When polarized light travels or propagates within the chamber 60 along the first optical orientation 72, the polarized light can scatter within the chamber 60. As stated above, scattered light detected at a right angle to the direction of propagation of the polarized incident light has a linear polarization. Therefore, the detector 62 detects fluoresced light within a second optical zone 78 of the chamber 60 where the second optical zone 78 is oriented at a substantially 90 degree angle relative to the first optical zone 70. By manipulating the relative orientation of the detector 62 relative to the plane of scattered light, the fluorescence signal from the gas sample relative to the undesirable scatter signal is optimized. Additionally, by removing what would otherwise be the favorable scattering plane of light from the source, the scattered light resulting from particle interaction is reduced.

As indicated above, the fluorescence quenching reduction mechanism is configured to reduce the effect of fluorescence quenching on the fluorescence of the elemental mercury 55 within the sample 32. In one arrangement, the fluorescence quenching reduction mechanism includes a pressure reduction apparatus 54 coupled to the housing 50. The pressure reduction apparatus 54 reduces the pressure of the fluid sample 32 relative to that of a fluid source, such as the stack or flue 34 of a coal combustion facility or converter 24 as illustrated in FIG. 1, to minimize or reduce fluorescence quenching of the elemental mercury 55 within the fluid sample 32.

With reference to FIG. 2, in one arrangement the pressure reduction apparatus 54 includes a vacuum pump 92 operating in conjunction with the flow restrictor 39 of the housing 50. As illustrated, the outlet 58 of the housing 50 is in fluid communication with the vacuum pump 92. The inlet 56 of the housing is configured as, or includes, a flow restrictor 39 (e.g., a nozzle) that defines a relatively narrow width or diameter 94, relative to a width or diameter of the heated conduit 40. During operation, for example, the vacuum pump 92 draws the fluid sample 32 from a fluid source, such as the converter 24, and into the housing 50 of the analyzer 26 through the flow restrictor 39 of the housing 50. As the fluid sample 32 flows through the flow restrictor 39 (e.g., the flow restrictor of the inlet 56), the pressure of the fluid sample 32 decreases from a first pressure of approximately 1 atmosphere (e.g., as contained within the converter 24) to a second pressure between approximately 0.1 and 0.3 atmospheres (e.g., as contained within the analyzer 26). The chamber 60 of the analyzer 26, therefore, contains the gas sample 32 at a negative gage pressure.

As indicated above, collisional deactivation can cause fluorescence quenching of elemental mercury within a fluid or gas sample. In the process of collisional deactivation, an excited mercury atom collides with another atom/molecule within the gas sample or with a wall of the analyzer 26 and transfers energy with the object of the collision without emitting light—i.e., the excited elemental mercury atom surrenders its energy through a non-fluorescent mechanism. In the present analyzer 26, use of a flow-restricted inlet and the vacuum pump 92 results in a low pressure of the gas sample 32 within the analyzer 26, reducing the number of atoms (e.g., mercury atoms) within the chamber 60 and reducing the number of atomic/molecular interactions of the excited mercury atoms within the chamber 60. Therefore, the analyzer 26 reduces the effect of collisional deactivation and, therefore, fluorescence quenching on the fluorescence of the elemental mercury 55.

The quenching of mercury fluorescence follows the classical Stem-Volmer equation when mercury concentrations are sufficiently low. This condition is met in the present analyzer 26 for detection of trace levels of mercury. For a gas sample 32 containing a constant fraction, or mixing ratio, of mercury diluted in another gas, the fluorescence intensity changes with pressure according to the following equation:

$$F(M,p) = C^*(p/(1+\phi_M^* p))$$

where $F(M, p)$=Fluorescence intensity of mercury in mixing gas M at pressure p

C=Constant depending on the mixing ratio p=Sample pressure $\phi_M$=Quenching coefficient for mixing gas M The relative fluorescence intensity of mercury in the gas sample, compared to a gas sample at 1 atmosphere absolute pressure is calculated from:

$$F(M,p)/F(M_{Ref}, 1 \text{ atm}) = (p^*(1+\phi_{MRef}))/(1+\phi_M^* p)$$

where $M_{Ref}$=Reference mixing gas.

In the case where the reference mixing gas is air, the quenching coefficient for air is $\phi_{Air}$=140/atmosphere. In the case where the reference mixing gas is nitrogen the quenching coefficient for nitrogen is, $\phi_{Nitrogen}$=18/atmosphere.

Figure 3:
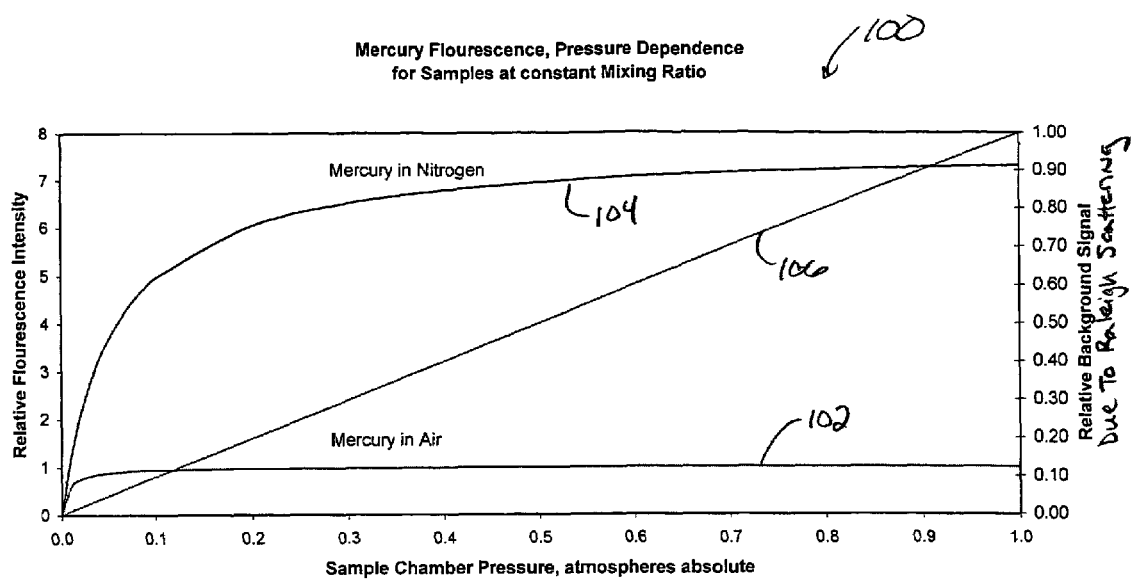
FIG. 3 illustrates relationships between relative fluorescence intensity and sample chamber pressure.

FIG. 3 is a graph 100 that illustrates relationships (e.g., the Stern—Volmer relationship) between relative fluorescence intensity and sample chamber pressure (e.g., sample chamber pressure relative to a reference of air at 1 atmosphere pressure) for mixtures of mercury in air and mercury in nitrogen. A first curve 102 represents a relationship between relative fluorescence intensity and sample chamber pressure for a gas sample 32 with mixtures of mercury in air. A second curve 104 represents a relationship between relative fluorescence intensity and sample chamber pressure for a gas sample 32 with mixtures of mercury in nitrogen.

FIG. 3 shows that for mercury in air (represented as the first curve 102), the high or upper pressure limit is reached at approximately 0.1 atmospheres. Above this pressure, the effect of an increase in the number of absorbing mercury atoms with increasing pressure is cancelled by an equivalent increase in the rate of quenching of the increased number of excited state mercury atoms which are produced. As a consequence, little increase in fluorescence signal can be obtained by increasing the air sample pressure beyond 0.1 atmospheres. Conversely, little fluorescence signal is lost by operating the analyzer sample chamber 60 under a partial vacuum and reducing the sample pressure from atmospheric pressure to 0.1 atmospheres absolute pressure.

The graph 100 shows that the sample pressure for mixtures in air can be reduced to 0.1 atmospheres without significant reduction in fluorescence intensity. The graph 100 also includes a third curve 106 that represents a relationship between relative background signal caused by scattering of light by air/nitrogen molecules due to Raleigh scattering and sample chamber pressure. As shown, the scattering of excitation energy by the air/nitrogen molecules (e.g., Raleigh scattering) is reduced proportionally relative to a reduction in pressure. For example, at a pressure of 0.1 atmospheres, the relative background signal is reduced to approximately $\frac{1}{10}$ of the value at 1 atmosphere pressure. That is, a reduction in pressure within the chamber 60 has the effect of greatly reducing the background signal, which is present even when there is no mercury in the sample gas. The reduced intensity of background signal or light allows for the detection of relatively low levels of mercury vapor, thereby enhancing the Lower Detectable Limit (LDL) of the mercury monitoring system 20.

FIG. 3 also shows the effect of diluting the sample with nitrogen rather than air, as indicated by the second curve 104. At an operating pressure of 0.1 atmospheres, for example, the fluorescence intensity is increased by approximately a factor of five. This increase occurs with little change in the scattered light intensity. The background intensity is thus reduced five fold compared to the fluorescence signal, yielding a further improvement in the LDL for mercury.

Figure 4:
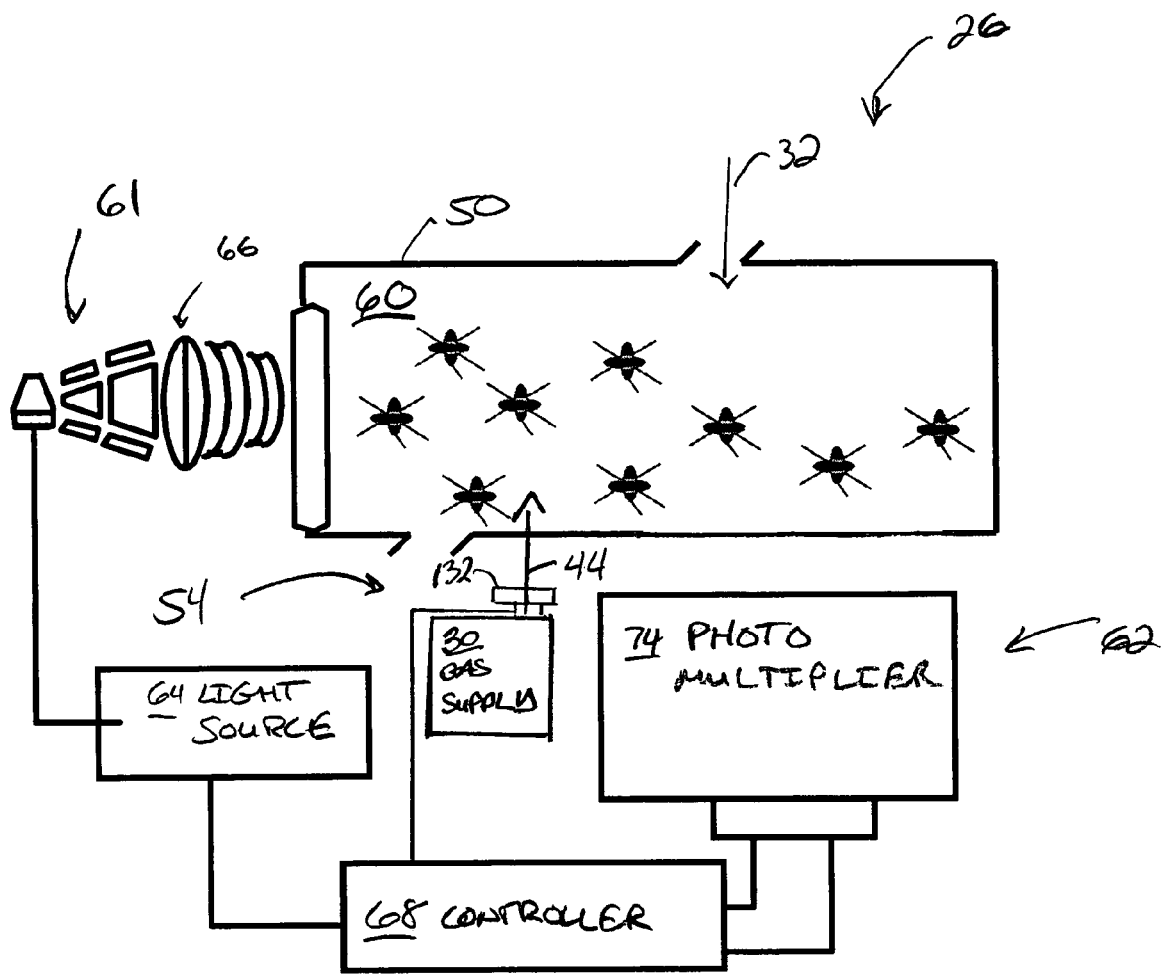
FIG. 4 illustrates an arrangement of a mercury analyzer as used within the mercury monitoring system of FIG. 1.

FIG. 4 illustrates another arrangement of the analyzer 26. As illustrated, the fluorescence quenching reduction mechanism 54 of the analyzer 26 is configured as the gas supply 30 (e.g., an oxygen depleted gas source) containing oxygen depleted gas, such as pure nitrogen gas. In one arrangement, the oxygen depleted gas source 30 delivers the oxygen depleted gas to the chamber 60 of the analyzer 26 via the conduit 44. In another arrangement, the oxygen depleted gas source 30 delivers the oxygen depleted gas to the probe 22 via the conduit 47 (e.g., as indicated in FIG. 1). Oxygen depleted gases, such as pure nitrogen gas, quench the fluorescence of elemental mercury significantly less than oxygen. Introduction of an oxygen depleted gas into the chamber 60 dilutes the fluid sample 32 and reduces fluorescence quenching of elemental mercury within the gas sample 32. Also, introduction of an oxygen depleted gas into the probe 22 dilutes the fluid sample 32 and reduces fluorescence quenching of elemental mercury within the gas sample 32.

In one arrangement, a valve assembly 132 is positioned between the oxygen depleted gas source 30 and the housing 50 to regulate the amount of oxygen depleted gas delivered from the source 30, and the valve assembly 132 is electrically coupled to the controller 68. The controller 68 regulates opening and closing of the valve assembly 132 to control the amount of oxygen depleted gas delivered to the chamber 60 or to the probe 22.

Figure 5:
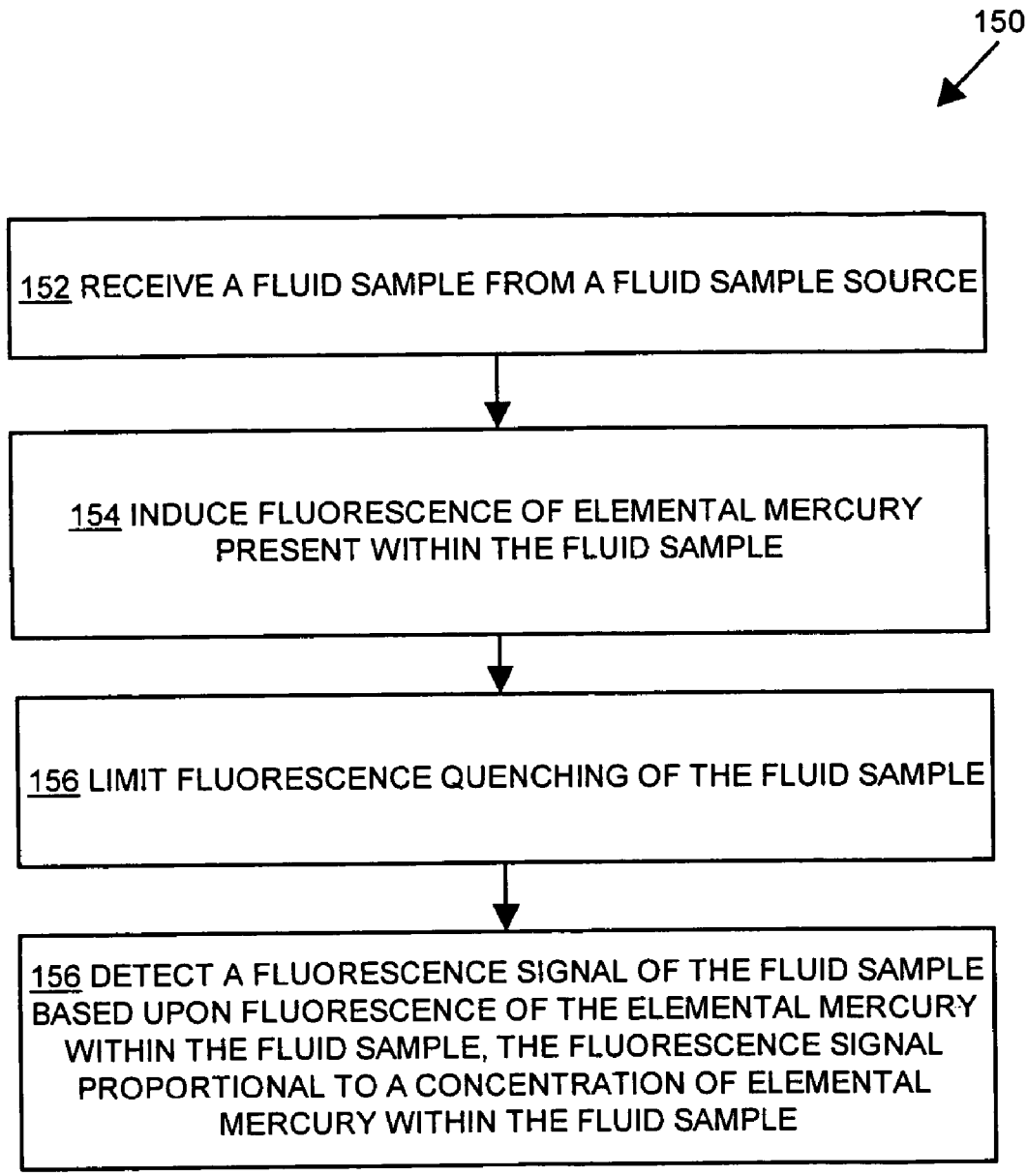
FIG. 5 is a flow chart of a procedure performed by the mercury analyzer.

FIG. 5 is a flow chart 150 of a procedure performed by the mercury analyzer 26 during operation when detecting elemental mercury 55 in a fluid sample 32.

In step 152, the analyzer 26 receives a fluid sample 32 from a fluid sample source. For example, in one arrangement, the analyzer 26 receives the fluid sample 32 from a converter 24 that converts oxidized forms of mercury into elemental mercury. In one arrangement, the analyzer 26 receives the fluid sample 32 from a stack or flue 34 of a coal combustion facility.

In step 154, the analyzer 26 induces fluorescence of elemental mercury present within the fluid sample 32. For example, the light source assembly 61 of the analyzer 26 produces light at a wavelength of approximately 253.7 nm to induce fluorescence of elemental mercury within the gas sample 32.

In step 156, which may occur concurrently with step 154, the analyzer 26 limits fluorescence quenching of the fluid sample. In one arrangement, the analyzer 26 decreases the pressure of the fluid sample 32 within chamber 60, relative to the pressure of the fluid sample 32 at the fluid sample source. For example, the inlet 56 of the housing is configured as, or includes, a flow restrictor (e.g., a nozzle) that defines a relatively narrow width or diameter 94. As a vacuum pump 92 draws the fluid sample 32 from the sample source and through the inlet, the pump 92 and configuration of the inlet 56 reduces the pressure of the fluid sample within the chamber 60. Such reduction of pressure reduces the effect of collisional deactivation on fluorescence of the elemental mercury within the fluid sample 32. In another arrangement, the analyzer 26 receives an oxygen depleted gas (e.g., pure nitrogen gas) from an oxygen depleted gas source 128. The oxygen depleted gas dilutes the oxygen-based gas within the fluid sample 32. Such dilution, in turn, reduces fluorescence quenching on the elemental mercury fluorescence within the gas sample 32.

In step 158, the analyzer 26 detects a fluorescence signal of the fluid sample 32 based upon fluorescence of the elemental mercury 55 within the fluid sample 32, the fluorescence signal proportional to a concentration of elemental mercury 55 within the fluid sample 32. For example, the detector assembly 62 of the analyzer 26 receives a fluorescence signal from fluid sample 32 as generated by fluorescing of elemental mercury 55 within gas sample. Based upon the fluorescence signal, the detector assembly 62 calculates a concentration level for the fluid sample and provides an output, such as to a user or operator.

The analyzer 26 performs the method over real-time in a substantially continuous manner. For example, the analyzer detects the elemental mercury concentration of a gas sample at a particular rate (e.g., once every second) and provides the concentration result as an output from the analyzer at the particular rate. As a fluid sample 32 flows into the analyzer 26 at a substantially continuous rate, the analyzer 26 performs the real time mercury concentration analysis of the fluid sample 32. Thus the analyzer 26 can detect "spikes" in the concentration of elemental mercury 55 present within the fluid sample or trends (e.g., an increase or decrease) relating to the mercury concentrations within the sample over time.

As indicated above, reducing the pressure within the analyzer 26 (e.g., via the pressure reduction apparatus) causes the number of molecular collision of the elemental mercury 55 to drop. However, the number of excited elemental mercury molecules available to fluoresce is proportional to the pressure. Therefore, a pressure reduction of the gas sample 32 also reduces the number of excited elemental mercury molecules available to fluoresce. By containing the fluid sample 32 under a vacuum or negative gage pressure, the analyzer 26 reduces the fluorescence intensity or signal produced by the excited elemental mercury 55 within the fluid sample 32 during fluorescence of the excited elemental mercury 55. However, while the effect of reduced pressure on the gas sample 32 places greater demands on detection sensitivity, fluorescence detection according to the invention provides a substantially sensitive and accurate method for detecting the concentration of elemental mercury within a fluid sample.

While this invention has been particularly shown and described with references to preferred embodiments thereof, it will be understood by those skilled in the art that various changes in form and details may be made therein without departing from the spirit and scope of the invention as defined by the appended claims.

Figure 6:
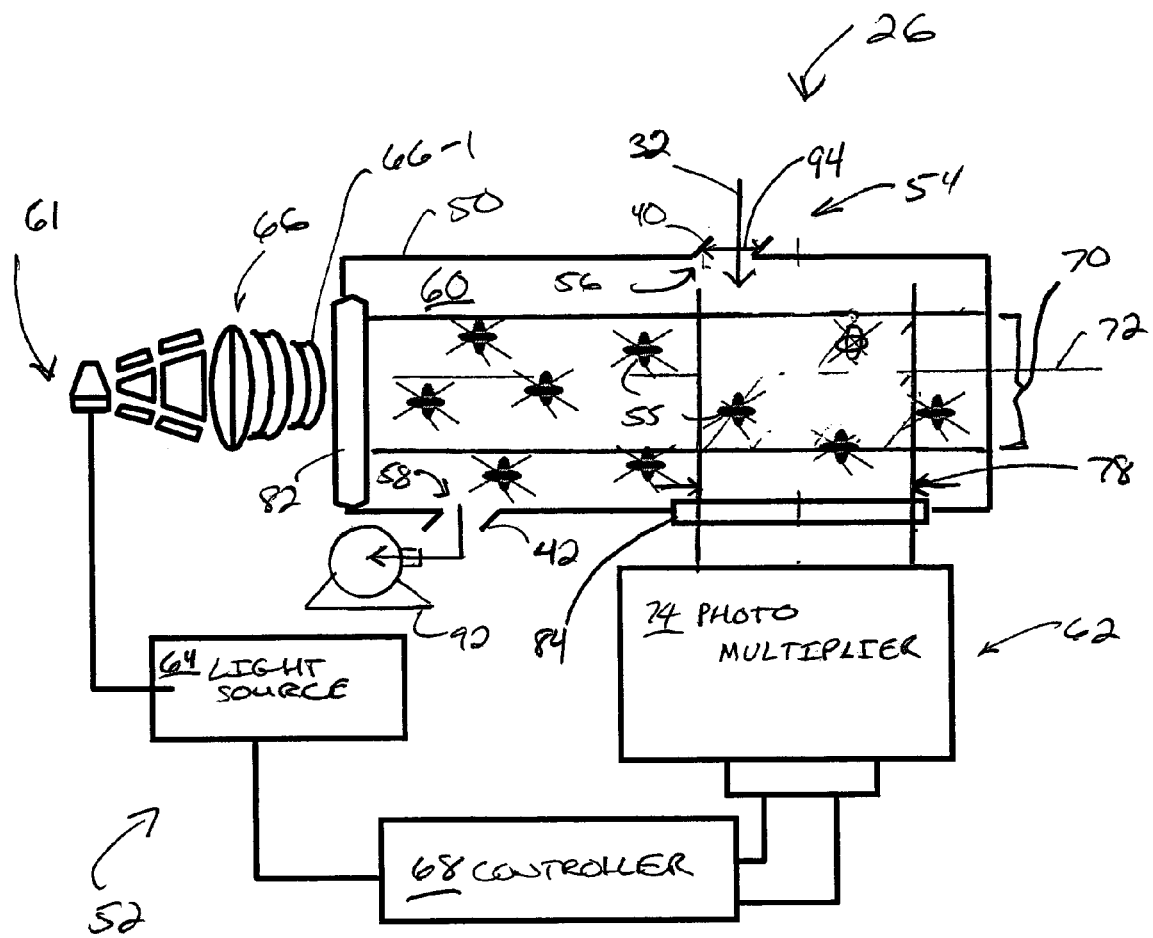
FIG. 6 illustrates another arrangement of a mercury analyzer as used within the mercury monitoring system of FIG. 1.

For example, as described above with respect to FIG. 2, the analyzer 26 includes an input polarized filter 82 associated with the light assembly. Such description is by way of example only. In one arrangement, as illustrated in FIG. 6, the analyzer 26 includes a first polarizing filter 82 and a second polarizing filter 86 where the polarizing filters 82, 84 are crossed relative to each other and relative to a favored scattering plane. As indicated above, the use of a single polarizing filter 82 reduces the effect of light scattering within the chamber 60 as caused by interaction of the light with the gas within the chamber 60. The use of crossed polarizing filters 82, 84 minimize the effect of other types of optical interferences formed within the analyzer 26. For example, the crossed polarizing filters 82, 84 minimizes the effects of light reflected from the walls of the chamber on the output signal (e.g., fluorescence) detected by the a detector assembly 62.

As indicated above, the analyzer 26 includes a fluorescence quenching reduction mechanism 54 configured as either a pressure reduction apparatus or as an oxygen depleted gas source 128. In one arrangement, the fluorescence quenching reduction mechanism 54 is formed as the combination of the pressure reduction apparatus 90(e.g., the pump 92 and the flow restrictor 39) and the oxygen depleted gas source 128 so as to further reduce the effect of quenching on the fluorescence of elemental mercury 55 within the gas sample 32.

As indicated above, with reference to FIG. 2, the pressure reduction apparatus 54 includes a vacuum pump 92 operating in conjunction with a flow restrictor 39 (e.g., a nozzle) where the inlet 56 of the housing 50 includes the flow restrictor 39. In one arrangement, the flow restrictor 39 orients upstream from the inlet 56 of the analyzer 26.

What is claimed is:

1. An elemental mercury analyzer comprising:
   a housing having an inlet for receiving a fluid sample from a fluid source, an outlet for discharging the fluid sample, and defining a chamber for containing the fluid sample;

a fluorescence assembly in optical communication with the chamber, the fluorescence assembly configured to induce fluorescence of elemental mercury present within the fluid sample and detect a fluorescence signal of the fluid sample based upon fluorescence of at least a portion of the elemental mercury;

a pressure reduction apparatus in fluid communication with the chamber, the pressure reduction apparatus operable to reduce the pressure of the fluid sample, relative to the pressure of the fluid source, to reduce fluorescence quenching of the sample; and a source of oxygen depleted gas in fluid communication with the chamber via a port other than the inlet, the source of oxygen depleted gas operable to reduce fluorescence quenching of the fluid sample.

2. The elemental mercury analyzer of claim 1 wherein the pressure reduction apparatus comprises a pump operable to draw a fluid sample into the chamber via the inlet and a flow restrictor for restricting flow of the fluid sample prior to its entry into the chamber.

3. The elemental mercury analyzer of claim 2 further comprising:
   light baffling material within the chamber to reduce scattering of light within the chamber.

4. The elemental mercury analyzer of claim 3, wherein the pressure reduction apparatus is configured to maintain the chamber at a pressure between 0.1 and 0.3 atmospheres of pressure.

5. The elemental mercury analyzer of claim 4, wherein the fluorescence assembly includes a light source to produce light and induce the fluorescence of elemental mercury in the chamber, the elemental mercury analyzer further comprising:
   at least one convex type lens and polarizing light filter to collimate and polarize the light produced by the light source and fluoresce the elemental mercury in an optical zone of the chamber.

6. The elemental mercury analyzer of claim 1 wherein the fluorescence assembly comprises a light source assembly configured to induce fluorescence of elemental mercury present within the fluid sample and a detector assembly configured to detect the fluorescence signal of the fluid sample based upon fluorescence of at least a portion of the elemental mercury.

7. The elemental mercury analyzer of claim 6 wherein the light source assembly comprises an input polarizing element oriented in optical communication with the light source assembly.

8. The elemental mercury analyzer of claim 7 wherein the detector assembly comprises an output polarizing element oriented in optical communication with the detector assembly.

9. The elemental mercury analyzer of claim 8 wherein the input polarizing element of the light source assembly defines a first optical orientation substantially orthogonal to a favored plane of particle scattered light.

10. The elemental mercury analyzer of claim 1 wherein the pressure reduction apparatus is operable to reduce the pressure of a fluid sample, relative to the pressure of the fluid source, to reduce an effect of Raleigh scattering within the fluid sample.

* * * * *